(12) United States Patent
Owen

(10) Patent No.: US 12,226,278 B2
(45) Date of Patent: *Feb. 18, 2025

(54) ORTHODONTIC TREATMENT SYSTEM

(71) Applicant: KLOwen Braces, Inc., Lakeway, TX (US)

(72) Inventor: Brandon Owen, Lakeway, TX (US)

(73) Assignee: KLOwen Braces, Inc., Lakeway, TX (US)

( * ) Notice: Subject to any disclaimer, the term of this patent is extended or adjusted under 35 U.S.C. 154(b) by 270 days.

This patent is subject to a terminal disclaimer.

(21) Appl. No.: 17/734,022

(22) Filed: Apr. 30, 2022

(65) Prior Publication Data

US 2023/0054809 A1 Feb. 23, 2023

Related U.S. Application Data

(63) Continuation of application No. 15/937,290, filed on Mar. 27, 2018, now Pat. No. 11,331,165.

(51) Int. Cl.
| | |
|---|---|
| *A61C 7/00* | (2006.01) |
| *A61C 7/14* | (2006.01) |
| *A61C 7/18* | (2006.01) |
| *A61C 7/28* | (2006.01) |
| *A61C 9/00* | (2006.01) |

(Continued)

(52) U.S. Cl.
CPC ............... *A61C 7/002* (2013.01); *A61C 7/146* (2013.01); *A61C 7/18* (2013.01); *A61C 7/28* (2013.01); *A61C 7/148* (2013.01); *A61C 9/006* (2013.01); *A61F 2/30942* (2013.01); *B33Y 80/00* (2014.12)

(58) Field of Classification Search
None
See application file for complete search history.

(56) References Cited

U.S. PATENT DOCUMENTS

| 2,716,283 A | 8/1955 | Atkinson |
| 3,250,003 A | 5/1966 | Collito |

(Continued)

FOREIGN PATENT DOCUMENTS

| EP | 1 830 735 | 9/2007 |
| WO | WO 2007/087697 | 8/2007 |

(Continued)

OTHER PUBLICATIONS

United States Provisional U.S. Appl. No. 61/880,322, filed Sep. 20, 2013.

(Continued)

*Primary Examiner* — Heidi M Eide
(74) *Attorney, Agent, or Firm* — Craig R. Miles; CR MILES P.C.

(57) ABSTRACT

A computer system and computerized method in which orthodontic treatment, including midcourse correction of one or more teeth in a dental arch fitted with a dental appliance, comprises a virtual simulation of a dental arch fitted with a virtual dental appliance in which each of the one or more teeth can be discretely moved from an initial position to a final position allowing modification of the fitted dental appliance by computerized selection of one or more brackets and production of a bonding tray adapted to hold the selected brackets in correspondence to determined bracket bonding locations in the virtual simulation of dental arch.

14 Claims, 12 Drawing Sheets

(51) Int. Cl.
   *A61F 2/30*       (2006.01)
   *B33Y 80/00*      (2015.01)

(56) References Cited

U.S. PATENT DOCUMENTS

| | | | |
|---|---|---|---|
| 3,946,488 A | 3/1976 | Miller et al. | |
| 3,964,165 A | 6/1976 | Stahl | |
| 4,139,945 A | 2/1979 | DiGiulio | |
| 4,209,906 A | 7/1980 | Fujita | |
| 4,243,386 A | 1/1981 | Kawaguchi | |
| 4,487,581 A | 12/1984 | Adler | |
| 4,494,931 A | 1/1985 | Wildman | |
| 4,551,094 A | 11/1985 | Kesling | |
| 4,948,366 A | 8/1990 | Horn et al. | |
| 5,098,288 A | 3/1992 | Kesling | |
| 5,248,257 A | 9/1993 | Cannon | |
| 5,263,859 A | 11/1993 | Kesling | |
| 5,340,656 A | 8/1994 | Sachs et al. | |
| 5,387,380 A | 2/1995 | Cima et al. | |
| 5,447,432 A | 9/1995 | Andreiko et al. | |
| 5,464,347 A | 11/1995 | Allesee | |
| 5,464,349 A | 11/1995 | Andreiko et al. | |
| 5,542,842 A | 8/1996 | Andreiko et al. | |
| 5,683,243 A | 11/1997 | Andreiko et al. | |
| 5,782,631 A | 7/1998 | Kesling et al. | |
| 6,015,289 A | 1/2000 | Andreiko et al. | |
| 6,206,690 B1 | 3/2001 | Vargas | |
| 6,244,861 B1 | 6/2001 | Andreiko et al. | |
| 6,247,923 B1 | 6/2001 | Vashi | |
| 6,347,939 B2 | 2/2002 | Abels | |
| 6,394,798 B1 | 5/2002 | Huff et al. | |
| 6,554,613 B1 | 4/2003 | Sachdeva et al. | |
| 6,592,367 B2 | 7/2003 | Kyritsis | |
| 6,616,444 B2 | 9/2003 | Andreiko et al. | |
| 6,632,089 B2 | 10/2003 | Rubbert et al. | |
| 6,658,314 B1 | 12/2003 | Gothait | |
| 6,685,468 B1 | 2/2004 | Kesling | |
| 6,776,614 B2 | 8/2004 | Wiechmann et al. | |
| 7,033,170 B2 | 4/2006 | Cordato | |
| 7,037,382 B2 | 5/2006 | Davidson et al. | |
| 7,080,979 B2 | 7/2006 | Rubbert et al. | |
| 7,131,836 B1 | 11/2006 | Kesling | |
| 7,155,373 B2 | 12/2006 | Jordan et al. | |
| 7,160,107 B2 | 1/2007 | Kopelman et al. | |
| 7,168,950 B2 | 1/2007 | Cinader, Jr. et al. | |
| 7,223,099 B2 | 5/2007 | Niederwanger et al. | |
| 7,229,282 B2 | 6/2007 | Andreiko et al. | |
| 7,306,458 B1 | 12/2007 | Lu | |
| 7,326,051 B2 | 2/2008 | Miller | |
| 7,364,428 B2 | 4/2008 | Cinader, Jr. et al. | |
| 7,500,846 B2 | 3/2009 | Eshed et al. | |
| 7,604,768 B2 | 10/2009 | Kritchman | |
| 7,641,473 B2 | 1/2010 | Sporbert et al. | |
| 7,766,653 B2 | 8/2010 | Manemann et al. | |
| 7,837,466 B2 | 11/2010 | Griffith et al. | |
| 7,850,451 B2 | 12/2010 | Wiechmann et al. | |
| 8,113,828 B1 | 2/2012 | Greenfield | |
| 8,142,187 B2 | 3/2012 | Sporbert et al. | |
| 8,192,197 B2 | 6/2012 | Sporbert et al. | |
| 8,251,699 B2 | 8/2012 | Reising et al. | |
| 8,353,699 B2 | 1/2013 | Johnston | |
| 8,512,037 B2 | 8/2013 | Andreiko | |
| 8,550,814 B1 | 10/2013 | Collins | |
| 8,979,528 B2 | 3/2015 | Macchi et al. | |
| 9,326,831 B2 | 5/2016 | Cheang | |
| 9,345,553 B2 | 5/2016 | Andreiko et al. | |
| 9,387,055 B2 | 7/2016 | Cinader, Jr. et al. | |
| 9,414,897 B2 | 8/2016 | Wu et al. | |
| 9,486,299 B2 | 11/2016 | Owen | |
| 9,492,245 B2 | 11/2016 | Sherwood et al. | |
| 9,503,282 B2 | 11/2016 | Cody et al. | |
| 9,529,970 B2 | 12/2016 | Andreiko | |
| 9,642,678 B2 | 5/2017 | Kuo | |
| 9,707,057 B2 | 7/2017 | Owen | |
| 9,763,750 B2 | 9/2017 | Kim et al. | |
| 9,883,924 B2 | 2/2018 | Rudman | |
| 10,241,499 B1 | 3/2019 | Griffin | |
| 10,492,889 B2 | 12/2019 | Kim et al. | |
| 10,588,713 B2 | 3/2020 | Andreiko et al. | |
| 10,754,325 B1 | 8/2020 | Griffin, III | |
| 10,786,334 B2 | 9/2020 | Griffin, III et al. | |
| 11,234,798 B2 | 2/2022 | Dillion et al. | |
| 11,331,165 B2 | 5/2022 | Owen | |
| 2002/0010568 A1 | 1/2002 | Rubbert et al. | |
| 2002/0156652 A1 | 10/2002 | Sachdeva et al. | |
| 2003/0039938 A1 | 2/2003 | Orikasa | |
| 2003/0224310 A1 | 12/2003 | Andreiko | |
| 2004/0115586 A1 | 6/2004 | Andreiko et al. | |
| 2004/0121279 A1 | 6/2004 | Kelly | |
| 2004/0214128 A1 | 10/2004 | Sachdeva et al. | |
| 2004/0219471 A1 | 11/2004 | Cleary et al. | |
| 2005/0130095 A1* | 6/2005 | Raby | A61C 7/146 433/24 |
| 2005/0186525 A1 | 8/2005 | Abels et al. | |
| 2005/0244774 A1 | 11/2005 | Abels et al. | |
| 2006/0204918 A1 | 9/2006 | Voudouris | |
| 2006/0228662 A1 | 10/2006 | Lokar et al. | |
| 2006/0275731 A1 | 12/2006 | Wen et al. | |
| 2007/0128571 A1 | 6/2007 | Kimura | |
| 2007/0259300 A1 | 11/2007 | McLaghlin et al. | |
| 2007/0259302 A1 | 11/2007 | Jayawardena | |
| 2008/0057459 A1 | 3/2008 | Abels et al. | |
| 2008/0070184 A1 | 3/2008 | Farzin-Nia et al. | |
| 2008/0311534 A1 | 12/2008 | Farzin-Nia et al. | |
| 2009/0004617 A1 | 1/2009 | Oda et al. | |
| 2009/0004619 A1 | 1/2009 | Oda et al. | |
| 2009/0017410 A1 | 1/2009 | Raby et al. | |
| 2009/0098502 A1 | 4/2009 | Andreiko | |
| 2009/0117511 A1 | 5/2009 | Minium | |
| 2009/0155734 A1 | 6/2009 | Damon | |
| 2009/0162807 A1 | 6/2009 | Hagenganz et al. | |
| 2010/0106465 A1 | 4/2010 | Sporbert et al. | |
| 2010/0173256 A1 | 7/2010 | Rodriguez et al. | |
| 2010/0196839 A1 | 8/2010 | Stevens | |
| 2010/0260405 A1 | 10/2010 | Cinader, Jr. | |
| 2010/0297569 A1 | 11/2010 | Huang et al. | |
| 2011/0004331 A1 | 1/2011 | Cinader, Jr. et al. | |
| 2011/0014583 A1 | 1/2011 | Romano et al. | |
| 2011/0020762 A1 | 1/2011 | Kanomi et al. | |
| 2011/0033811 A1 | 2/2011 | Swain | |
| 2011/0091832 A1 | 4/2011 | Kim et al. | |
| 2011/0097682 A1 | 4/2011 | Curiel et al. | |
| 2011/0151391 A1 | 6/2011 | Shih et al. | |
| 2011/0250556 A1 | 10/2011 | Heiser | |
| 2012/0015315 A1 | 1/2012 | Wiechmann et al. | |
| 2012/0107760 A1 | 5/2012 | Eichenberg | |
| 2012/0225398 A1 | 9/2012 | Fallah | |
| 2012/0308952 A1 | 12/2012 | Cosse | |
| 2012/0322019 A1 | 12/2012 | Lewis | |
| 2013/0040260 A1 | 2/2013 | Bukhary | |
| 2013/0309625 A1 | 11/2013 | Macchi et al. | |
| 2013/0325431 A1 | 12/2013 | See et al. | |
| 2015/0099237 A1 | 4/2015 | Owen | |
| 2015/0132707 A1 | 5/2015 | Huang et al. | |
| 2015/0245983 A1 | 9/2015 | Lorentz et al. | |
| 2017/0079748 A1 | 3/2017 | Andreiko | |
| 2017/0224442 A1 | 8/2017 | Kuo | |
| 2017/0281316 A1 | 10/2017 | Owen | |
| 2018/0116766 A1 | 5/2018 | Owen | |
| 2018/0303583 A1 | 10/2018 | Tong et al. | |
| 2019/0102880 A1 | 4/2019 | Parpara et al. | |
| 2019/0209269 A1* | 7/2019 | Gualano | A61C 7/145 |
| 2019/0328493 A1 | 10/2019 | Griffin, III et al. | |
| 2020/0275992 A1 | 9/2020 | Shannon et al. | |
| 2020/0401104 A1 | 12/2020 | Griffin, III | |
| 2020/0405446 A1 | 12/2020 | Shannon et al. | |
| 2021/0015593 A1 | 1/2021 | Shannon et al. | |
| 2021/0077224 A1 | 3/2021 | Griffin, III et al. | |
| 2021/0077227 A1 | 3/2021 | Griffin, III et al. | |

(56) References Cited

U.S. PATENT DOCUMENTS

2021/0401546 A1     12/2021    Gardner
2023/0049287 A1      2/2023    Fisker

FOREIGN PATENT DOCUMENTS

WO     WO 2011/068601 A1    6/2011
WO     WO 2012/116877 A1    9/2012
WO     WO 2015/052541 A1    4/2015

OTHER PUBLICATIONS

PCT International Patent Application No. PCT/US2014/056679; International Search Report dated Jan. 2, 2015, 15 total pages.
PCT International Patent Application No. PCT/US2014/056679, filed Sep. 19, 2014.
PCT International Patent Application No. PCT/US14/58982, filed Oct. 3, 2014.
PCT International Patent Application No. PCT/US14/58982; International Search Report dated Jan. 14, 2015, 10 total pages.
U.S. Appl. No. 61/886,461, filed Oct. 3, 2013.
U.S. Appl. No. 15/648,305, filed Jul. 12, 2017.
U.S. Appl. No. 14/504,325, filed Oct. 1, 2014.
U.S. Appl. No. 15/711,996, filed Sep. 21, 2017.
Itero. Making a Great First Impression . . . Website, http://www.itero.com, originally downloaded Nov. 13, 2017, 2 pages.
Itero. Optimized Invisalign Connectivity. Website, http://www.itero.com, originally downloaded Nov. 13, 2017, 2 pages.
Ormco. Insignia™ Advanced Smile Design™. Website, https://ormco.com, originally downloaded Nov. 13, 2017, 3 pages.
Ormco. Insignia Approver Interface (Ai). Website, https://ormco.com, originally downloaded Nov. 13, 2017, 3 pages.
OrthoSelect. DIBS-OrthoSelect. Website, https://www.myorthoselect.com, originally downloaded Nov. 13, 2017, 6 pages.
U.S. Appl. No. 15/847,718, filed Dec. 19, 2017.
PCT International Patent Application No. PCT/US18/22167, International Search Report and Written Opinion of the International Searching Authority dated Jun. 4, 2018, 16 pages.
PCT International Patent Application No. PCT/US18/49616, International Search Report and Written Opinion of the International Searching Authority dated Nov. 30, 2018, 12 pages.
PCT International Patent Application No. PCT/US19/13350; International Search Report and Written Opinion of the International Searching Authority dated Apr. 22, 2019, 8 pages.
European Patent Application No. 14845595.9, European Supplementary Search Report dated Oct. 20, 2017, 6 pages.
European Patent Application No. 14850598.5, Extended European Search Report dated Apr. 21, 2017, 7 pages.
European Patent Application No. 18820788.0, Extended European Search Report dated Jan. 20, 2021, 7 pages.
European Patent Application No. 18820788.0, Office Action dated Oct. 12, 2021, 6 pages.
PCT International Patent Application No. PCT/US24/18707, International Search Report and Written Opinion of the International Searching Authority dated Jun. 26, 2024, 9 pages.
U.S. Appl. No. 15/937,290, Office Action mailed Jun. 18, 2019.
U.S. Appl. No. 15/937,290, Office Action mailed Dec. 11, 2019.
U.S. Appl. No. 15/937,290, Office Action mailed Jun. 15, 2020.
U.S. Appl. No. 15/937,290, Office Action mailed Dec. 4, 2020.
U.S. Appl. No. 15/937,290, Office Action mailed Aug. 26, 2021.

* cited by examiner

ORTHODONTIC TREATMENT SYSTEM

This United States patent application is a continuation of U.S. patent application Ser. No. 15/937,290, filed Mar. 27, 2018, now U.S. Pat. No. 11,331,165, issued May 17, 2022, hereby incorporated by reference herein.

FIELD OF THE INVENTION

A computer system and computerized method in which orthodontic treatment, including midcourse correction of one or more teeth in a dental arch fitted with a dental appliance, comprises a virtual simulation of a dental arch fitted with a virtual dental appliance in which each of the one or more teeth can be discretely moved from an initial position to a final position allowing modification of the fitted dental appliance by computerized selection of one or more brackets to be affixed at determined bracket bonding locations and production of a bonding tray adapted to hold the selected brackets in correspondence to determined bracket bonding locations in the virtual simulation of dental arch and when engaged to the matching portions of the dental arch correctly positions each of the one or more brackets at the determined bracket bonding locations on the respective one or more teeth.

BACKGROUND OF THE INVENTION

Orthodontic treatment involves movement of malocclused teeth to desired locations in the oral cavity. One common type of orthodontic treatment involves the use of small, slotted orthodontic appliances known as brackets. The brackets are fixed to the patient's teeth and an archwire is placed in the slot of each bracket. The archwire forms a track to guide movement of the teeth to desired locations. The ends of orthodontic archwires are often connected to small orthodontic appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly and collectively referred to as a dental appliance or braces.

Typically, a braces prescription applies averaged values appropriate to reposition each tooth in the dental arch. As one example, the prescription for the maxillary central incisor will apply averaged values for thickness, torque, angulation, and rotation to reposition the tooth to an averaged position. Similarly, the maxillary lateral incisor will have a different thickness, torque, angulation, and rotation as will the maxillary canine and so on for each tooth in the respective dental arches. Unfortunately, the averaged values rarely deliver all of the teeth to the to an averaged ideal position for a variety of reasons, including: variation in tooth shape and size relative to the averaged tooth size, improper positioning of the bracket on the tooth, biological variation in tooth movement, and a difference in skeletal structure relative to the averaged patient.

Because very few patients have, for each and every tooth, a tooth shape or a skeletal makeup which matches the averaged value, a prescription applying averaged values may not properly reposition the teeth to the ideal averaged position even after transitioning through initial, intermediate, and final orthodontic wires. Currently, the failure to reposition a tooth to the average ideal position may be addressed either by removing the braces on teeth that are not in the ideal position and moving the braces on those teeth to a new position that will hopefully improve the position of these teeth. It may also be addressed by placing a bend or bends in the final orthodontic wire to alter the shape of the wire to correspondingly move the tooth along the altered shape of the wire toward the appropriate final position. In many instances, both of these methods may be concurrently repeatedly used to move all the teeth to an appropriate final position. These adjustments can extend the duration of time in orthodontic treatment.

Unlike conventional prescriptions that apply averaged values to reposition malocclused teeth, certain processes utilize one or more optical scanning technologies such as: confocal laser microscopy, active wavefront sampling, accordion fringe inferometry, optical coherent tomography, computer-aided design/computer-aided manufacturing, intraoral or a 3 dimensional x-ray to scan the teeth and to generate a digital model(s) of a dental arch which capture the unique tooth characteristics such as size and shape. The digital models can be analyzed to ideally position each of the teeth using a custom prescription based on the captured sizes, shapes, and other unique characteristics of the teeth. Certain conventional technologies utilize the custom prescription to fabricate a series of aligners serially applied to the teeth to incrementally reposition the teeth closer to their ideal position. Refinement can be executed by continued use of one or more optical technologies to generate updated digital models of the dental arches and refine the positions of the teeth that either did not reposition properly in the initial round of the aligners or did not achieve optimal esthetics or function.

Similarly, certain conventional technologies analyze digital models to control robot movement to bend orthodontic wires to a custom prescription based on the captured sizes, shapes, and other unique characteristics of the teeth. After placing the orthodontic wires, repositioning of the teeth can be evaluated, and if necessary, a new scan of the teeth can be obtained and new orthodontic wires can be ordered and placed on the brackets.

Unfortunately, mid-course corrections as above described can require significantly more time because the custom components must be manufactured, shipped, an applied to the teeth and can be more expensive than traditional orthodontic treatment.

SUMMARY OF THE INVENTION

One object of particular embodiments of the invention can be to provide a computerized method of midcourse orthodontic treatment including a virtual simulation of a dental arch fitted with a conventional dental appliance in which modification of the fitted dental appliance comprises identification and isolation of those teeth in the virtual simulation of the dental arch that fail to move to the ideal position, followed by computerized: 1) selection of brackets from a combinatorial library of available brackets, and 2) bracket location identification for the selected brackets on such teeth, based on analysis of the forces necessary to move the teeth to the ideal position in view of the location and prescription of the existing brackets on adjacent teeth.

Another object of particular embodiments of the invention can be to provide a digital model of a bracket or buccal tube positioning jig fabricated based on the virtual simulation of the dental arch and the computerized selection of brackets from a combinatorial library of available brackets, and the bracket location identification for the selected brackets on the malocclused teeth which are identified, isolated and repositioned in the virtual simulation of the dental arch to their ideal position. As to particular embodiments, the digital model of the bracket or buccal tube positioning jig can be analyzed by a three-dimensional object production application to generate computer executable instructions to operate a three-dimensional materials deposition apparatus in an additive build up process to produce a tangible bracket or buccal tube positioning jig. The bracket or buccal tube positioning jig can hold the selected brackets and be applied to the malocclused teeth which were identified, isolated and repositioned in the virtual simulation of the dental arch to properly position the selected brackets or buccal tubes on the malocclused teeth. The existing brackets or buccal tubes and adhesive for the malocclused teeth can be removed, the selected brackets or buccal tubes can be loaded in the positioning jigs and adhesive disposed onto the bracket base. The bracket or buccal tube positioning jig holding the brackets or buccal tubes can then positioned on the corresponding teeth. the adhesive can set, and the bracket or buccal tube positioning jig can be removed allowing placement the appropriate wire.

This method can allow for mid-course correction with efficiencies that can be created much more quickly and more economically than the current mid-course correction technologies.

Naturally, further objects of the invention are disclosed throughout other areas of the specification, drawings, photographs, and claims.

DETAILED DESCRIPTION OF THE INVENTION

Figure 1:
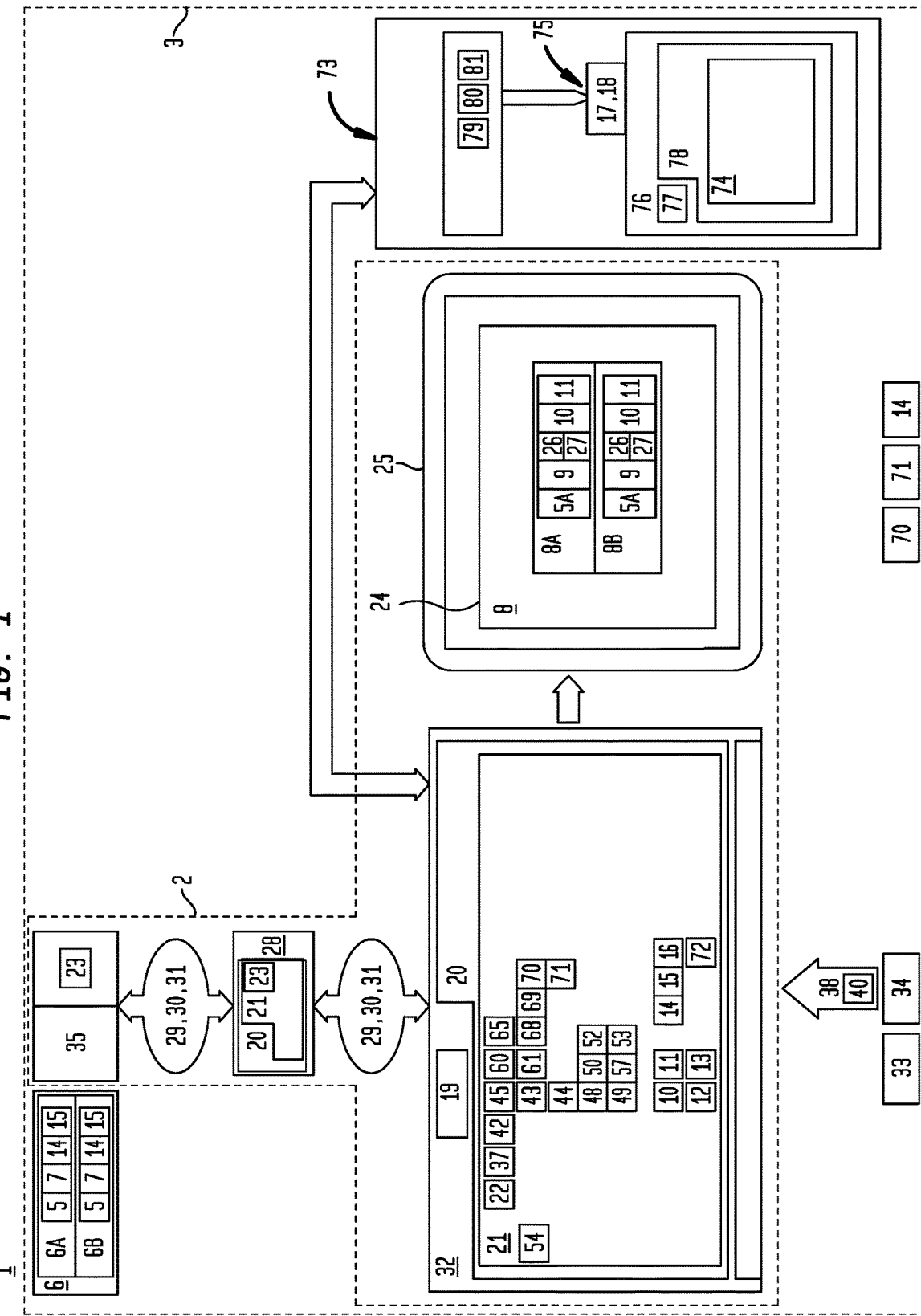
FIG. 1 is a block diagram of an inventive orthodontic treatment system including a computer system and a method in computer system to provide orthodontic treatment.

Now referring generally to FIGS. 1 through 13, which depict orthodontic apparatus and methods of an orthodontic treatment system (1). Specifically, a computer system (2) and computerized method (3) in which orthodontic treatment (4), including midcourse correction of one or more teeth (5) in a dental arch (6) fitted with a dental appliance (7)(also referred to as "braces"), comprises one or more of a virtual simulation of a dental arch (8) (also referred to as a "virtual dental arch") fitted with a virtual dental appliance (9)(also referred to as "virtual braces") with each of the one or more of the plurality of teeth (5) in the virtual simulation of the dental arch (8) discretely movable from an initial position (10) to a final position (11), which by computerized analysis of the movement in the virtual simulation of the dental arch (8), the current forces of correction (12) exerted by the fitted dental appliance (7) in the initial position (10) of the one or more teeth (5) in the virtual simulation of the dental arch (8) can be compared to prospective forces of correction (13) necessary to move each of the one or more teeth (5) to the final position (11) depicted in the virtual simulation of the dental arch (8) allowing modification of the fitted dental appliance (7) by computerized selection of one or more brackets (14) which correspondingly fitted to one or more teeth (5) in the dental arch (6) at determined bracket bonding locations (15) can deliver prospective forces of correction (13) to move the one or more teeth (5) in correspondence to the final position (11) depicted in the virtual simulation of the dental arch (8) and to generate one or more digital models (16) allowing production of corresponding tangible replica models (17) of the virtual simulation of the dental arch (8) or bonding trays (18) adapted to hold selected one or more brackets (14) in correspondence to determined bracket bonding locations (15) in the virtual simulation of dental arch (8) and when engaged to the matching portions of the dental arch (6) of a patient (P) correctly positions each of the one or more brackets (14) at the determined bracket bonding locations (15) on the respective one or more teeth (5).

Now referring primarily to FIG. 1, embodiments can include a processor (19) communicatively coupled to a non-transitory computer readable medium (20) containing computer executable instructions (21) (also referred to as the "orthodontic treatment application") which can, but need not necessarily, include a digital conversion module (22) which converts captured images (23) of a dental arch (6) including one or more of teeth (5) fitted with a dental appliance (7) into a virtual simulation of dental arch (8) which can be depicted on a display surface (24) of a display device (25). The virtual simulation of dental arch (8) can depict virtual brackets (26) which can include a virtual archwire (27) or can be depict the virtual simulation of dental arch (8) having virtual brackets (26) without the virtual archwire (27).

Again, referring primarily to FIG. 1, the non-transitory computer readable medium (20) can comprise one or more non-transitory computer readable media (20) residing in or distributed among one or more server computers (28) connected through one or more of a wide area network (29), such as the Internet (30) or a local area network (31) to one or more computer devices (32) including or consisting of: a network personal computer, a minicomputers, a slate, tablet or a pad computer, a hand-held computing device such as a smart phone, a camera/cell phone, or the like, or combinations thereof. The display surface (24) can be discrete from or incorporated into a computer device (32). The display surface (24) can, as illustrative examples, be a monitor screen, a display device, a touch screen, a mobile device, or other display surface (24), or combinations thereof, on which the virtual simulation of the dental arch (8) can be depicted for viewing by a computer user (33). Commands, information or indications (38) can be input by the user (33) to the computer device (32) through one or more input devices (34). Input devices (34) can, but need not necessarily, user (33) interactive devices including as examples: a keyboard, a pointing device such as a mouse; however, any method or device that converts user action into commands or information can be utilized including, as illustrative examples: a microphone, a joystick, a game pad, a touch screen, or an interactive screen.

Again, referring primarily to FIG. 1, in particular embodiments, the orthodontic treatment application (21) can, but need not necessarily, include a digital conversion module (22) executable to digitally convert captured images (23) of the dental arch (6). Captured images (23) of the dental arch can be achieved using a wide variety of existing and prospective optical technologies (35). As illustrative examples, one or more useful optical technologies (35) can include or consist of: computer-aided design/computer-aided manufacturing (also known as "CAD/CAM"), intraoral three-dimensional x-ray, confocal laser microscopy, active wavefront sampling, accordion fringe inferometry, optical coherent tomography, or the like, or combinations thereof.

Figure 2:
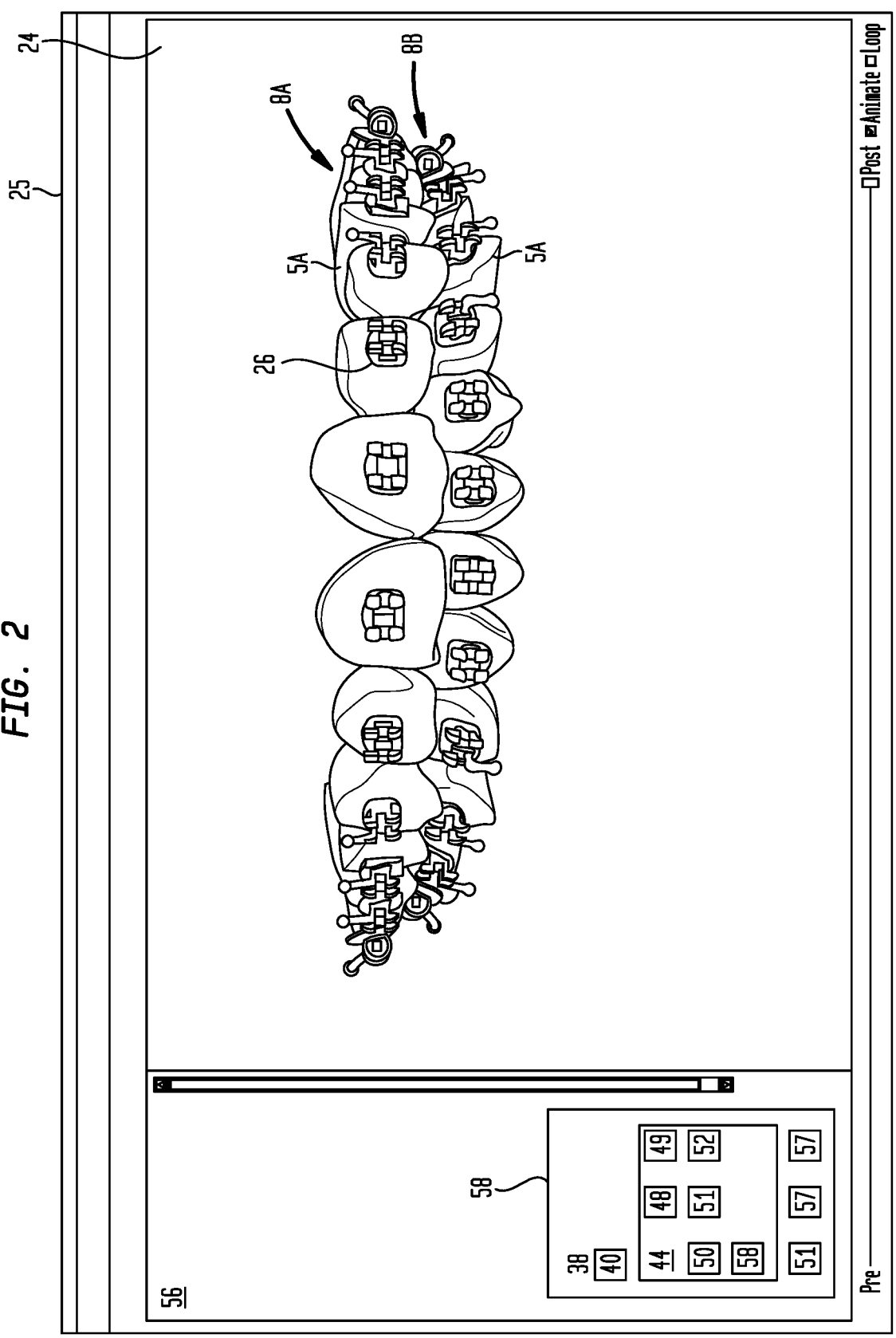
FIG. 2 is an illustration of an embodiment of a graphical user interface which depicts a virtual simulation of upper and lower dental arches each correspondingly including a plurality of teeth fitted only with brackets.
Figure 3:
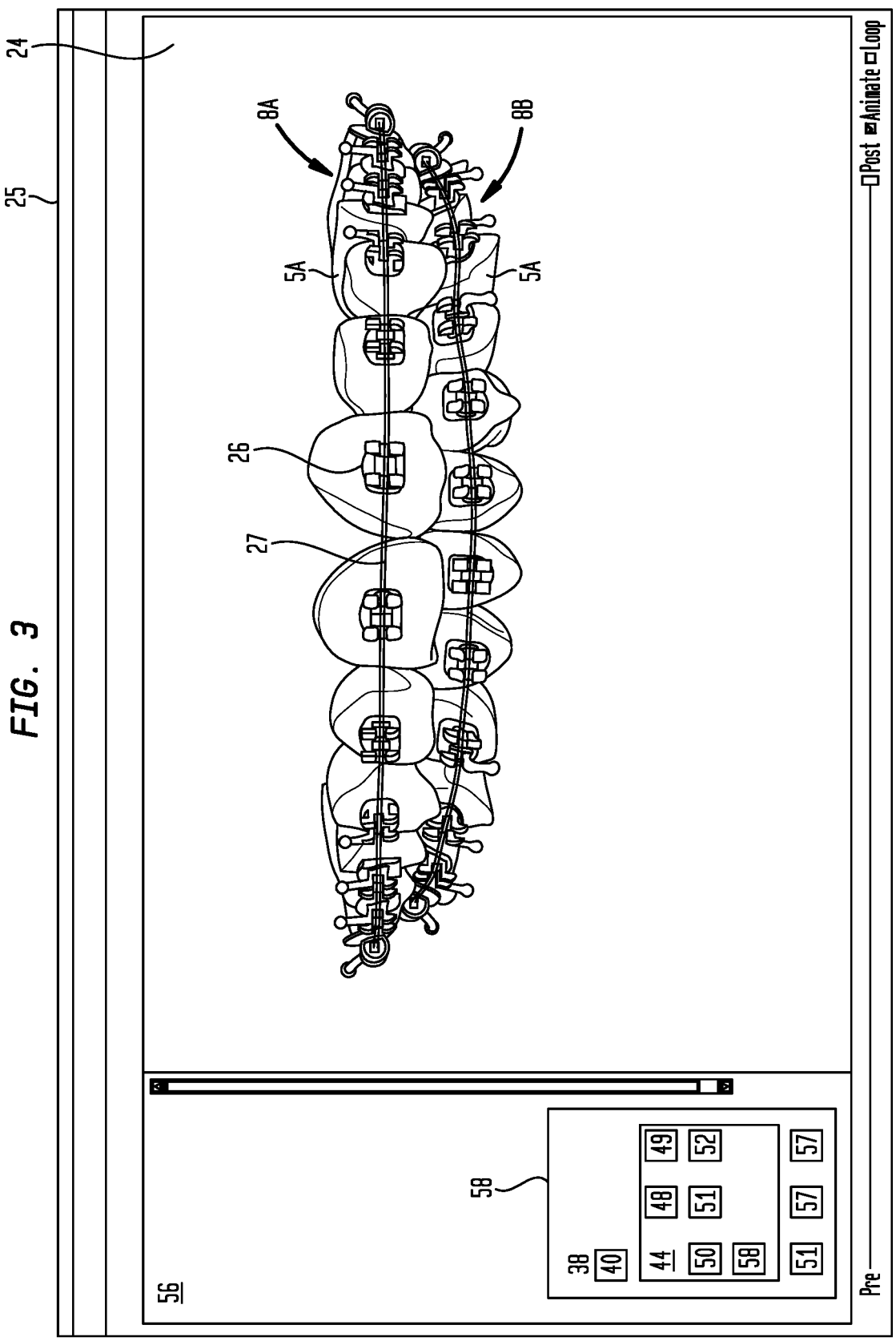
FIG. 3 is an illustration of an embodiment of a graphical user interface which depicts a virtual simulation of upper and lower dental arches each correspondingly including a plurality of teeth fitted with brackets and an archwire.

Again referring primarily to FIG. 1, the digital conversion module (22) operates to digitally convert captured images (23) of one or both of the upper and lower dental arches (6A)(6B) each correspondingly including a virtual plurality of teeth (5) fitted with braces (7) into a corresponding virtual simulation of the upper and lower dental arch (8A)(8B)(each including a virtual plurality of teeth (5A)) which can be depicted on the display surface (24) of the display device (24), with virtual brackets (26) and further including a virtual archwire (27) (as shown in the illustrative examples of FIGS. 2 and 3).

Figure 4:
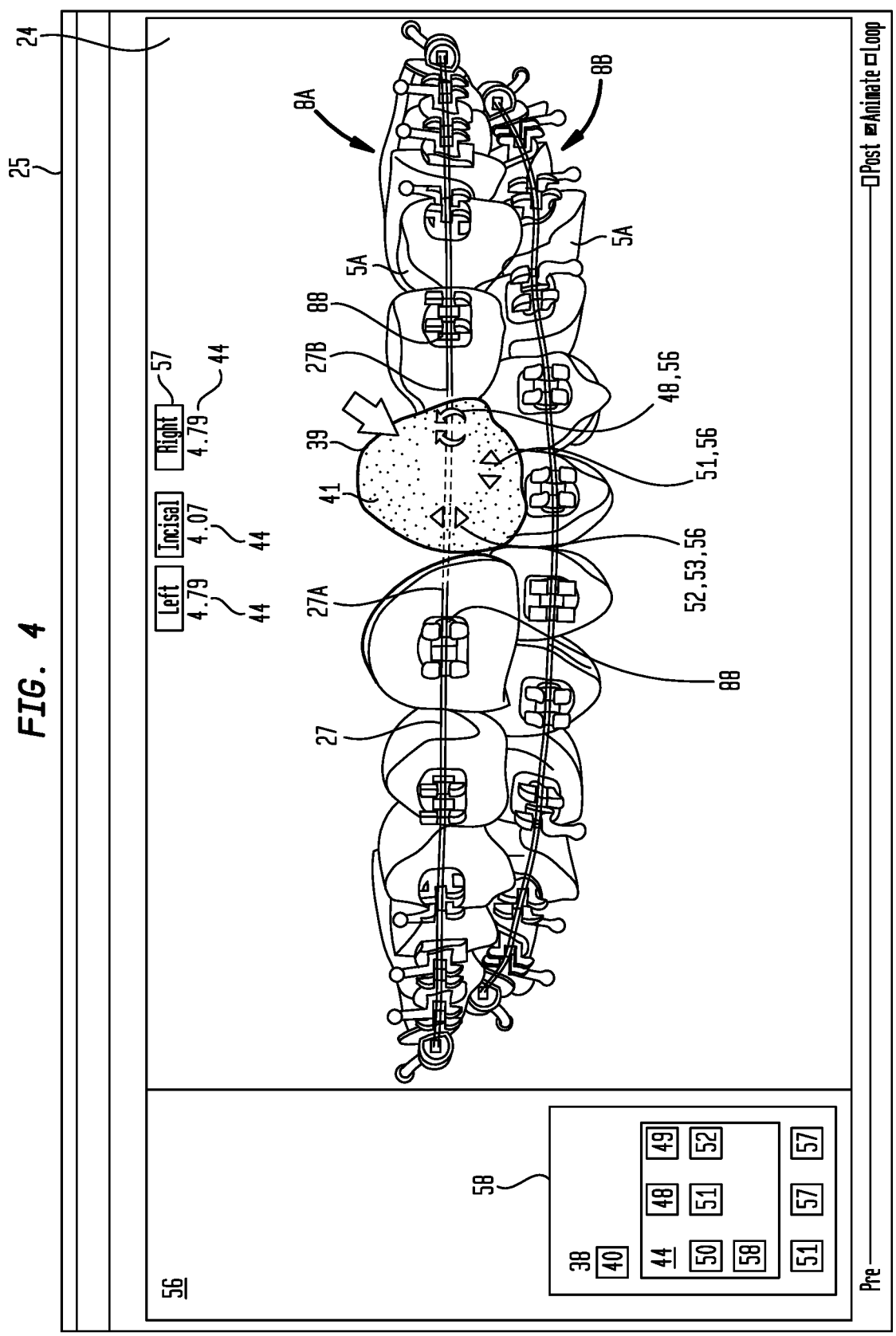
FIG. 4 is an illustration of an embodiment of a graphical user interface which depicts a virtual simulation of upper and lower dental arches each correspondingly including a plurality of teeth fitted with brackets and an archwire and by indications made in the graphical user interface a maxillary central incisor in the virtual simulation has been selected and segregated from the remaining teeth in virtual dental arch and the bracket and archwire removed.
Figure 5:
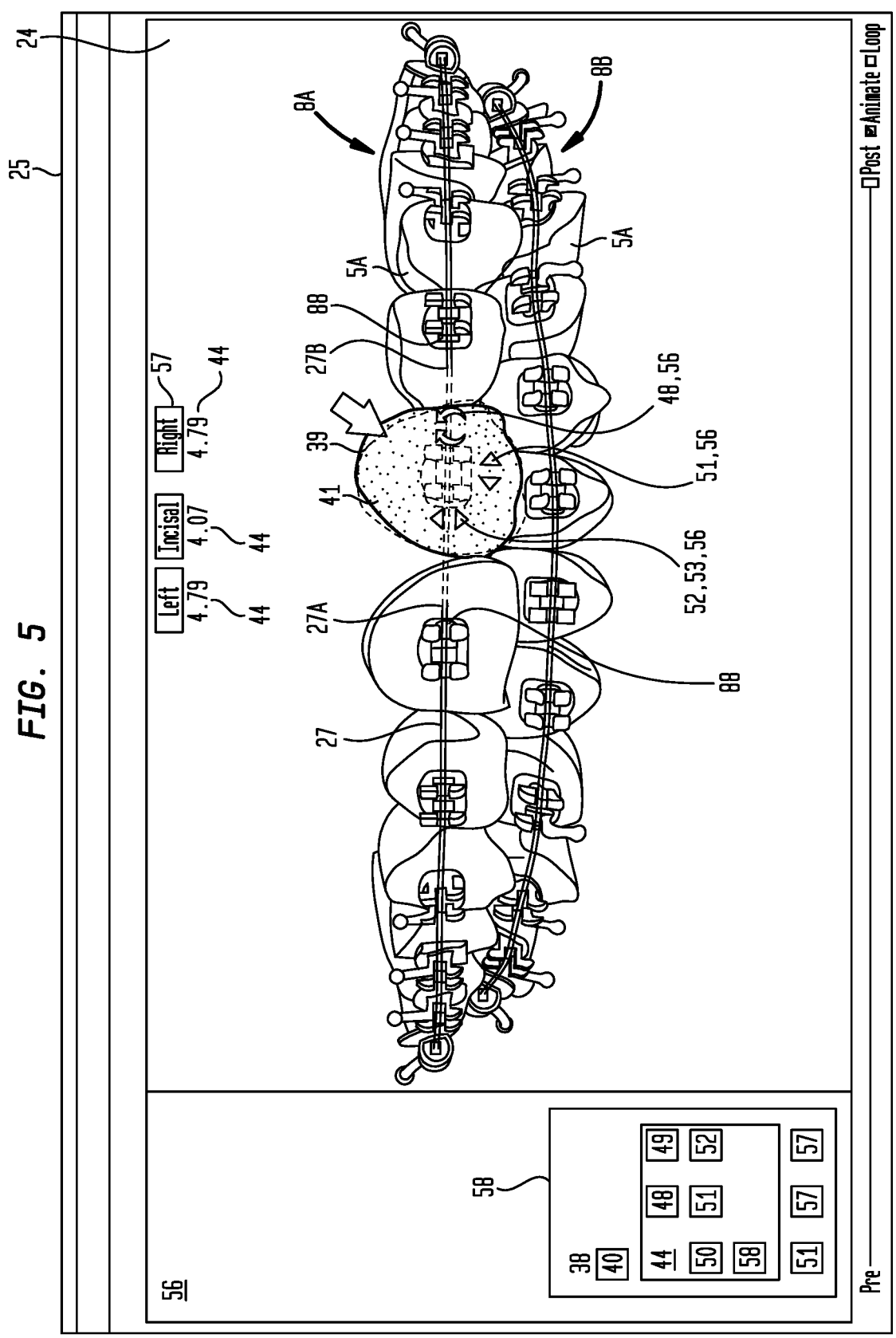
FIG. 5 is a depiction of a virtual simulation of the upper and lower dental arches shown in FIG. 4 with the selected and segregated tooth moved by indications in the graphical user interface to the final position allowing selection and placement of a virtual bracket on the selected segregated tooth (broken line indicating prior position in dental arch).
Figure 6:
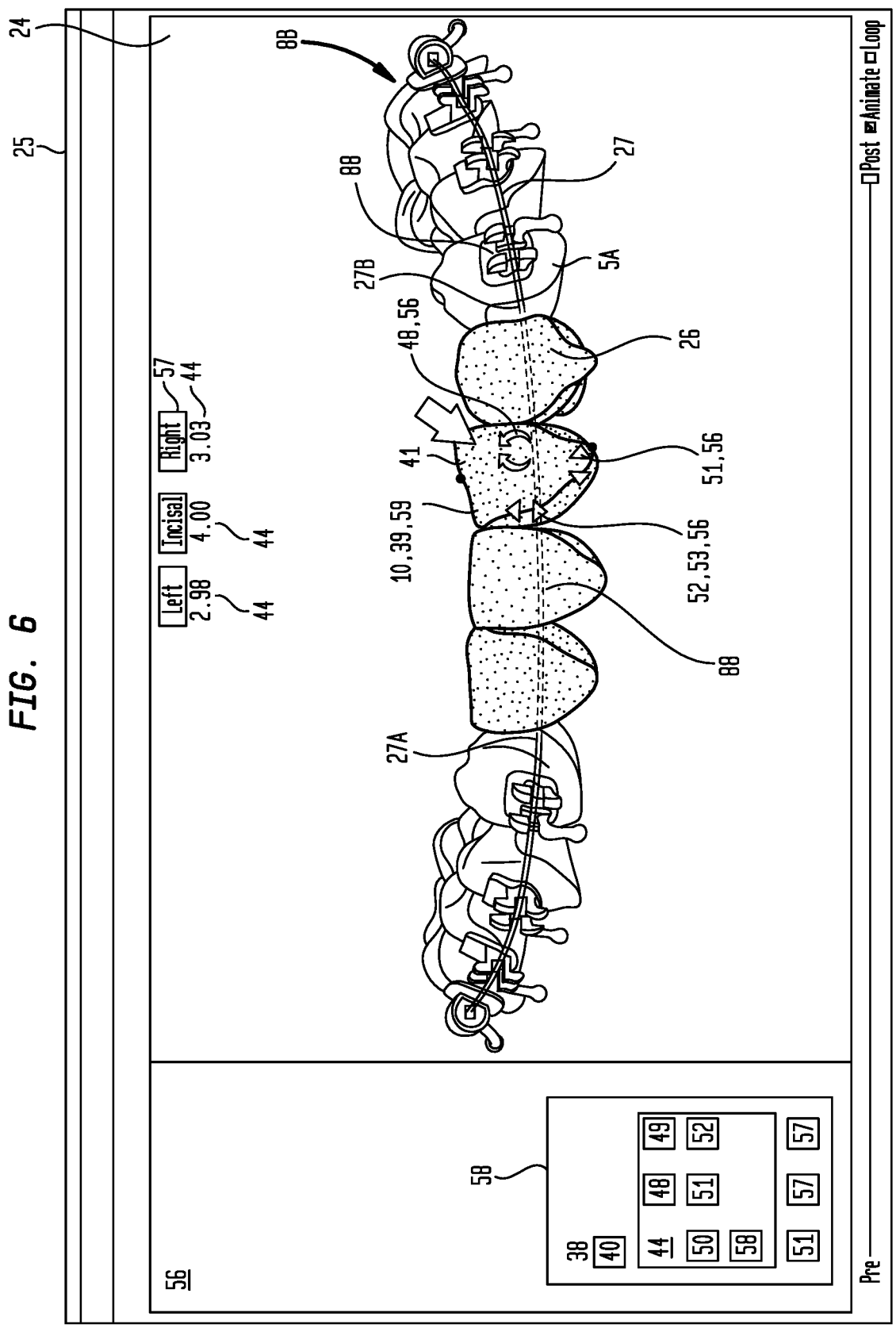
FIG. 6 is an illustration of an embodiment of a graphical user interface which depicts a virtual simulation of a lower dental arch including a plurality of teeth fitted with brackets and an archwire and by indications made in the graphical user interface the mandibular central incisors in the virtual simulation have been selected and segregated from the remaining teeth in virtual dental arch and the bracket and archwire removed.
Figure 7:
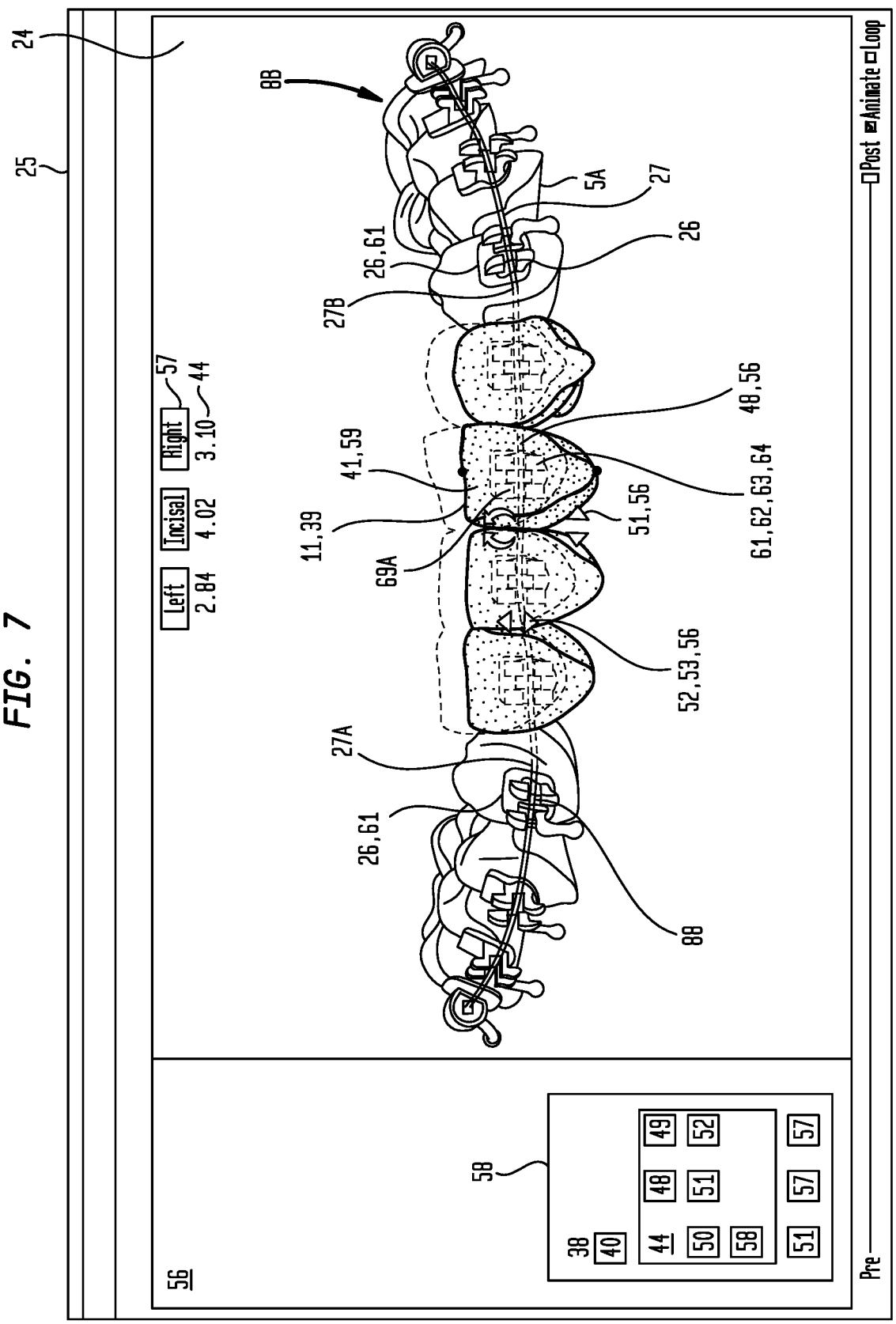
FIG. 7 is a depiction of a virtual simulation of the lower dental arch shown in FIG. 6 with the selected and segregated mandibular incisors moved by indications in the graphical user interface to the final position allowing selection and placement of virtual brackets on the selected segregated tooth (broken line indicating prior position in dental arch).
Figure 8:
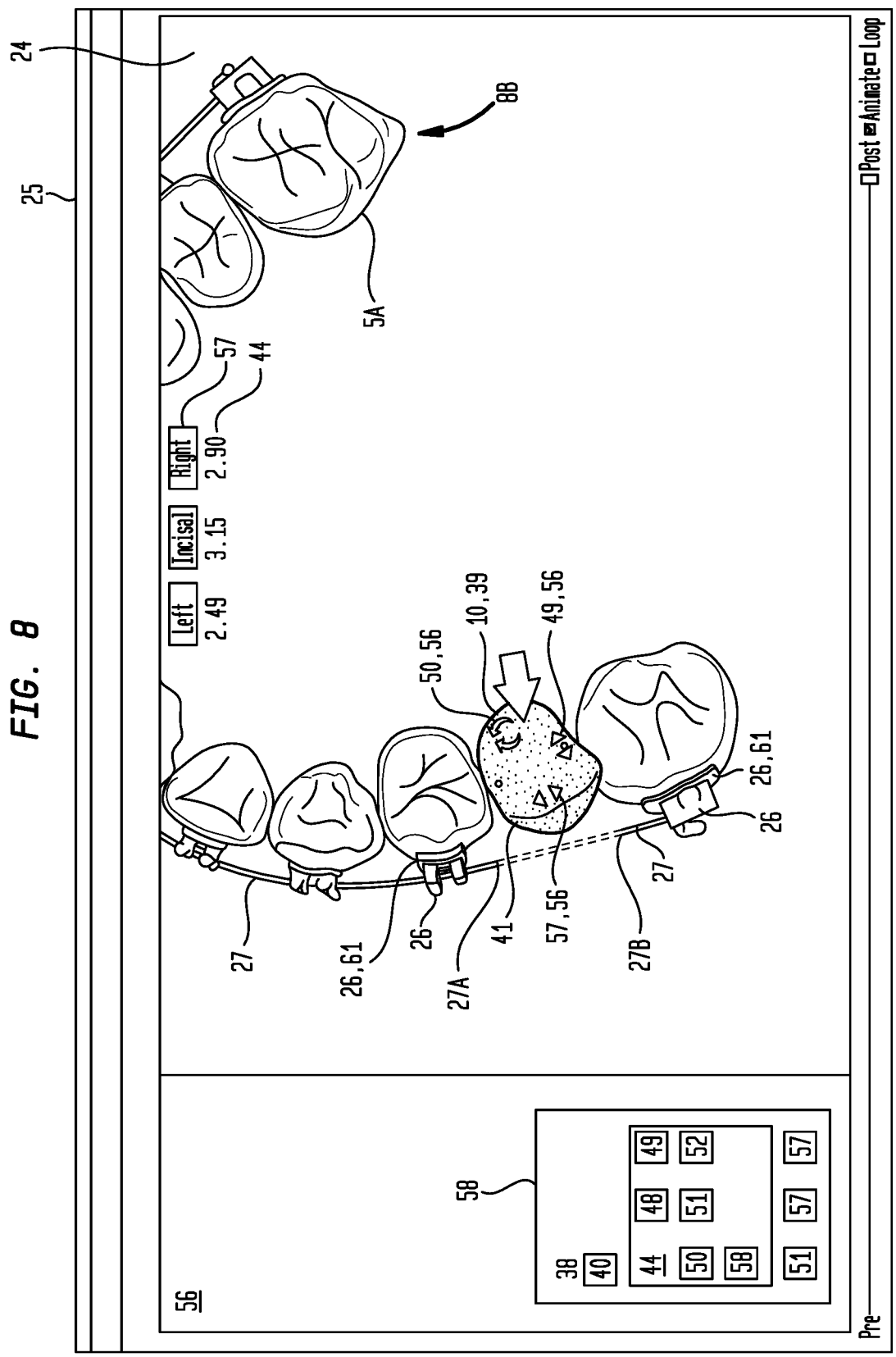
FIG. 8 is an illustration of an embodiment of a graphical user interface which depicts a virtual simulation of a lower dental arch including a plurality of teeth fitted with brackets and an archwire and by indications made in the graphical user interface the mandibular second molar in the virtual simulation has been selected and segregated from the remaining teeth in the virtual dental arch and the bracket and archwire removed.

Now referring generally to FIGS. 1 through 10, the virtual simulation can include one or more views of only the upper or lower dental arch (8A)(8B) (or both (8A) and (8B)) having the occlusal surfaces engaged or disengaged) including or consisting of one or more of: a labial view (as shown in the examples of FIGS. 2 through 4), an occlusal view (as shown in the example of FIG. 7 or 8) or a lingual view, whether serially presented as discrete images, or as, a plurality of views concurrently presented, whether side by side, superimposed, in multiple discrete presentation fields, animated or looped animation from pre-treatment dental arch to post-treatment dental arch to prospective treatment dental arch, or combinations thereof. For the purposes of this invention the term "virtual" means a simulant of an object made by processing computer executable instructions.

Now referring primarily to FIG. 1, in particular embodiments, the digital conversion module (22), or operation of the digital conversion module (22), can be omitted where digitized information including the virtual dental arch (8) (8A)(8B) can be accessed and retrieved for presentation on the display surface (24) without digital conversion. For example, a virtual dental arch (8) prior to orthodontic treatment can be retrieved over a wide area network (29) or a local area network (31) from one or more server computers (28) and a virtual dental arch (8) post orthodontic treatment, or any one or any plurality of virtual dental arches (8), can be depicted on the display surface (24) of the display device (25) discretely or concurrently (whether side by side, superimposed, in multiple discrete presentation fields, animated or looped animation from pre-treatment dental arch to post-treatment dental arch to prospective treatment dental arch, or combinations thereof). Now referring primarily to FIGS. 2 through 5, the upper and lower virtual dental arch (8A)(8B) can be depicted in the form of a bite registration (36).

Now referring primarily to FIGS. 1 and 4 through 9, particular embodiments of the orthodontic treatment application (21) can, but need not necessarily, include a tooth selection module (37) executable to allow selection of one or more of the virtual plurality of teeth (5A) in the virtual dental arch (8)(8A)(8B) by association of tooth selection indications (38) from an input device (34), such as: a pointer associated with a selected tooth (39) and click on a mouse button (as shown in the examples of FIGS. 4, 6 and 8), touch on the display surface over a selectable tooth (39), or entry of a tooth identification value (40), such as a numerical tooth identifier, or the like. In particular embodiments, the tooth selection module (37) can, but need not necessarily, further function to generate viewable selection indicia (41) to indicate or identify the selected tooth (39). Illustrative examples of viewable selection indicia (41) include one or more of increased weight of the outline of the selected tooth (39), stippled, shaded or colored highlight on the selected tooth (39), or the like.

Again, referring primarily to FIGS. 1 and 4 through 9, in particular embodiments, the orthodontic treatment application (21) can further include a tooth segregation module (42) which can be executed to segregate the selected tooth (39) from the remaining virtual plurality of teeth (5A) in the virtual dental arch (8)(8A)(8B) allowing the selected tooth (39) to be moved in the virtual dental arch (8)(8A)(8B) separate or distinct from the unselected virtual teeth in the virtual dental arch (8)(8A)(8B), and allowing corresponding analysis by the orthodontic treatment application (21) based on movement dependent rules (43) and malocclusion correction values (44) to be discretely associated with the selected tooth (39).

Figure 9:
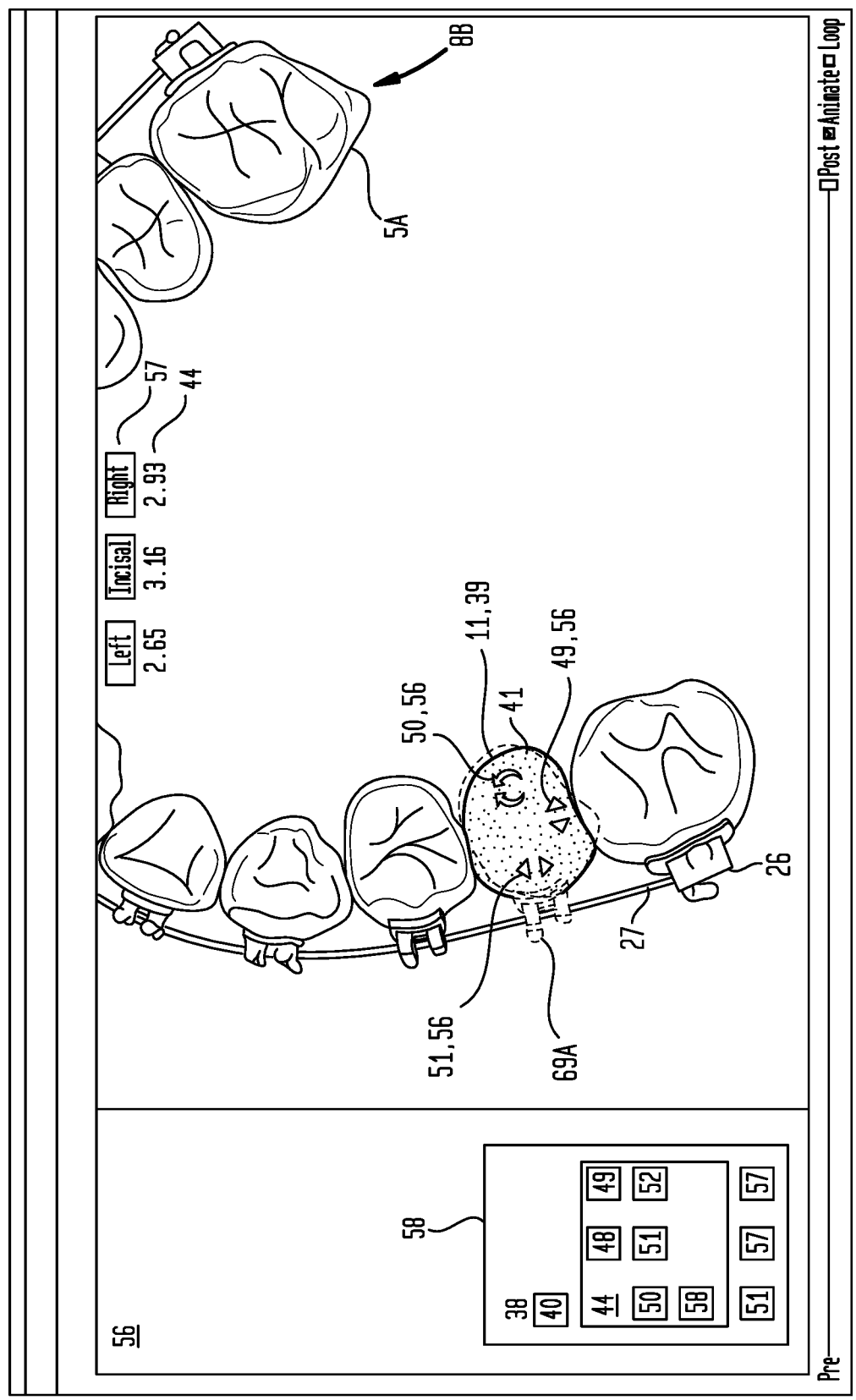
FIG. 9 is a depiction of a virtual simulation of the lower dental arch shown in FIG. 8 with the selected and segregated mandibular second molar moved by indications in the graphical user interface to the final position allowing selection and placement of virtual brackets on the selected segregated tooth (broken line indicating prior position in dental arch).

Now referring primarily to FIGS. 1 and 4 through 11, in particular embodiments, the orthodontic treatment application (21) can further include a tooth movement module (45) executable to allow movement of the segregated selected tooth (39) from an initial position (46) in the virtual dental arch (8)(8A)(8B)(as shown in the examples of FIGS. 4, 6 and 8) to a final position (11) in the virtual dental arch (8)(8A)(8B)(as shown in the examples of FIGS. 5, 7 and 9). Tooth movement for the purposes of this invention means any one or a combination of "tooth tipping (48)" in which the tooth crown of the tooth is tilted (as shown in the examples of FIGS. 4 and 5), "tooth torquing (49)" in which the crown of the tooth moves buccolingually (as shown in the in the examples of FIGS. 10 and 11), "tooth rotation (50)" in which the tooth rotates about the tooth longitudinal axis (as shown in the example of FIGS. 8 and 9), "tooth translation (51)" in which the tooth moves along the occlusal plane without changing the orientation along the tooth longitudinal axis, "tooth extrusion (52)" in which the tooth moves outward of the supporting structures, "tooth intrusion (53)" in which the tooth moves inward of the supporting structures (as shown in the example of FIGS. 6 and 7).

Again, referring primarily to FIGS. 1, and 2 through 11, in particular embodiments, the tooth movement module (45) can, but need not necessarily, be further executed to provide a user interface (54) in which malocclusion correction values (44) of tooth movement can be entered by interaction with the segregated selected tooth (39) in the virtual dental arch (8)(8A)(8B) on the display surface (24). As shown in the examples of FIGS. 4 and 8, malocclusion correction icons (56) representative of the corresponding movement can be superimposed or associated with the segregated selected tooth (39) for each of "tooth tipping (48)", "tooth torqueing (49)", "tooth rotation (50)", "tooth translation (51)", "tooth extrusion (52)", and "tooth intrusion (53)". Interaction with the malocclusion correction icons (56) generates the corresponding movement of the segregated selected tooth (39) in the virtual dental arch (8)(8A)(8B). In particular embodiments, the tooth movement module (45) can be further executed to present malocclusion correction value cells (57) on the display surface (24) and correspondingly present within the malocclusion correction value cells (57) the current malocclusion correction values (44) associated with the segregated selected tooth (39). In particular embodiments, the malocclusion correction values (44) can be modified by entry of malocclusion correction values (44) directly into the malocclusion correction value cells (57). For example, in the example of FIGS. 3 through 10, malocclusion correction value (44) for left, right and incisal tooth movement can be achieved by entry of malocclusion correction values (44) (which can be incremented in millimeters or other standard units) into the malocclusion correction value cells (57).

Again, referring primarily to FIGS. 1 and 2 through 11, in particular embodiments, the tooth movement module (45) can, but need not necessarily, further operate to provide a user interface (54) in which malocclusion correction values (44) can be entered by interaction with malocclusion correction icons (56) (each representative of a corresponding tooth movement) presented on the display surface (24) discrete from the presentation of the virtual dental arch (8)(8A)(8B). In particular embodiments, the malocclusion correction icons (56) can be disposed on the display surface (24) in a malocclusion correction icon field (58). Interaction with one or more of the malocclusion correction icons (56) can generate the corresponding movement of the segregated selected tooth (29) in the virtual dental arch (8)(8A)(8B). The tooth movement module (45) can further function to present malocclusion correction value cells (57) on the display surface (24) in the malocclusion correction icon field (58) and correspondingly within malocclusion correction value cells (57) present the current malocclusion correction values (44) associated with the segregated selected tooth (39). As shown in the example of FIGS. 5 and 6 by interaction with the malocclusion correction icons (56) presented in the malocclusion correction icon field (58), the right mandibular central incisor (59) has, in regard to tooth tipping (49 (50), been moved from an initial position (10) shown in the example of FIG. 5 to the final position (11) shown in the example of FIG. 7 with the corresponding change in malocclusion correction values (44) presented in the malocclusion correction value cells (57) presented in the malocclusion correction icon field (58).

Now referring primarily to FIGS. 1, 5, 7, 9, 10 and 11, in particular embodiments, the orthodontic treatment application (21) can further include a bracket bonding location module (60) which allows interaction with virtual brackets (26) depicted on the virtual dental arch (8)(8A)(8B) allowing adjustment of the virtual bracket bonding location (61) of the virtual brackets (26) on each segregated selected tooth (39). The bracket location module (60) can be executed prior to or subsequent to the tooth movement module (45). One or more of the bracket vertical position (62), bracket side to side position (63), bracket angulation (64) and position of the virtual bracket (26) relative to the virtual plurality of teeth (5A) in the opposing virtual dental arch (8A)(8B) can be adjusted by user (33) interaction with the virtual bracket (26) on each segregated selected tooth (39).

Figure 10:
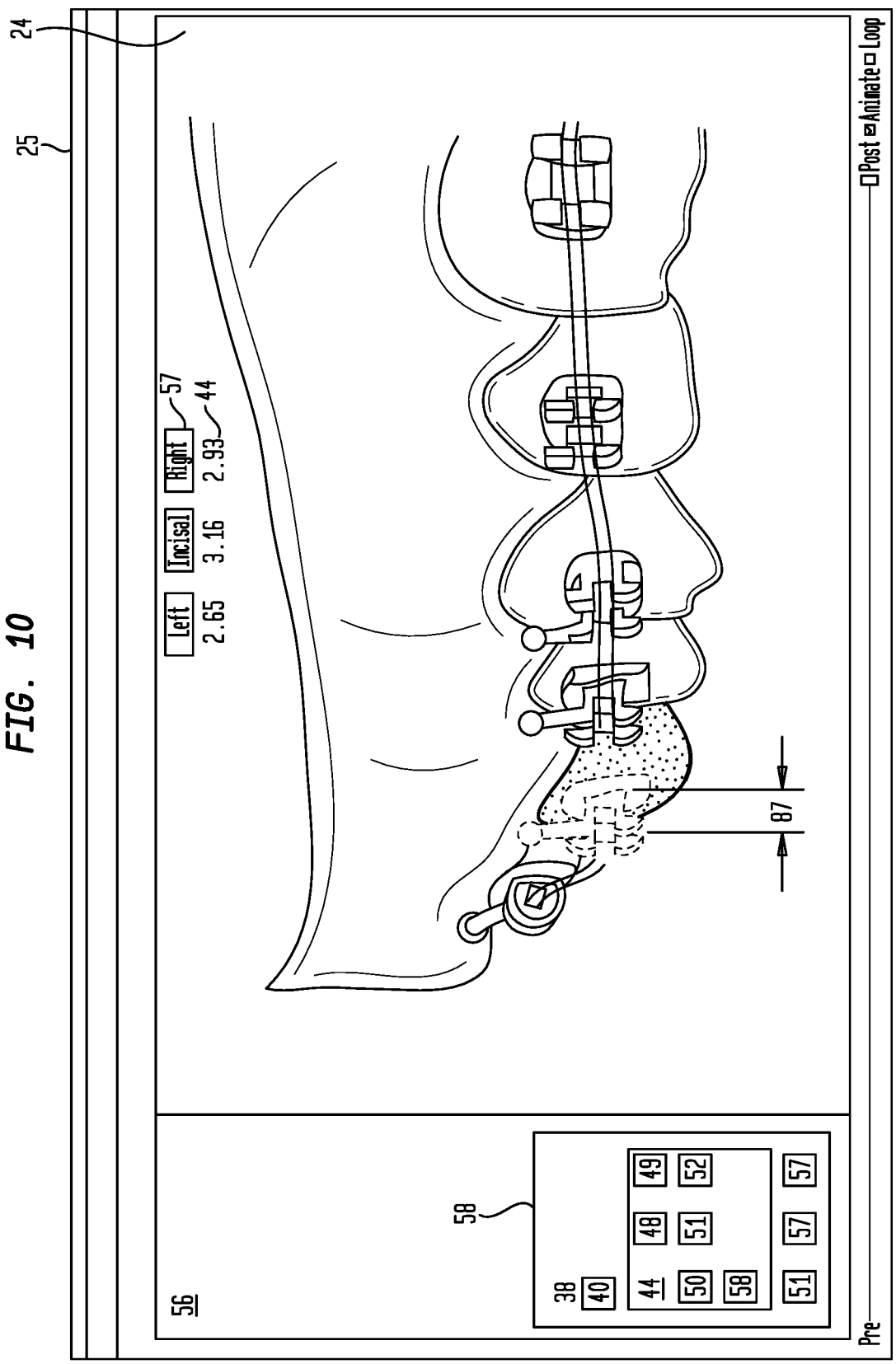
FIG. 10 is an illustration of an embodiment of a graphical user interface which depicts a virtual simulation of the upper arch including a selected and segregated tooth in the upper dental arch moved to the final position allowing selection and placement of a virtual bracket having a bracket body height determined by comparison to the prospective position of the virtual arch wire or the position of virtual bracket slots of the virtual brackets on the teeth adjacent the selected segregated tooth in the virtual simulation which in the corresponding orthodontic treatment of the patient's upper dental arch can apply corrective forces to move the tooth from the initial position to the final position shown in the virtual simulation.
Figure 11:
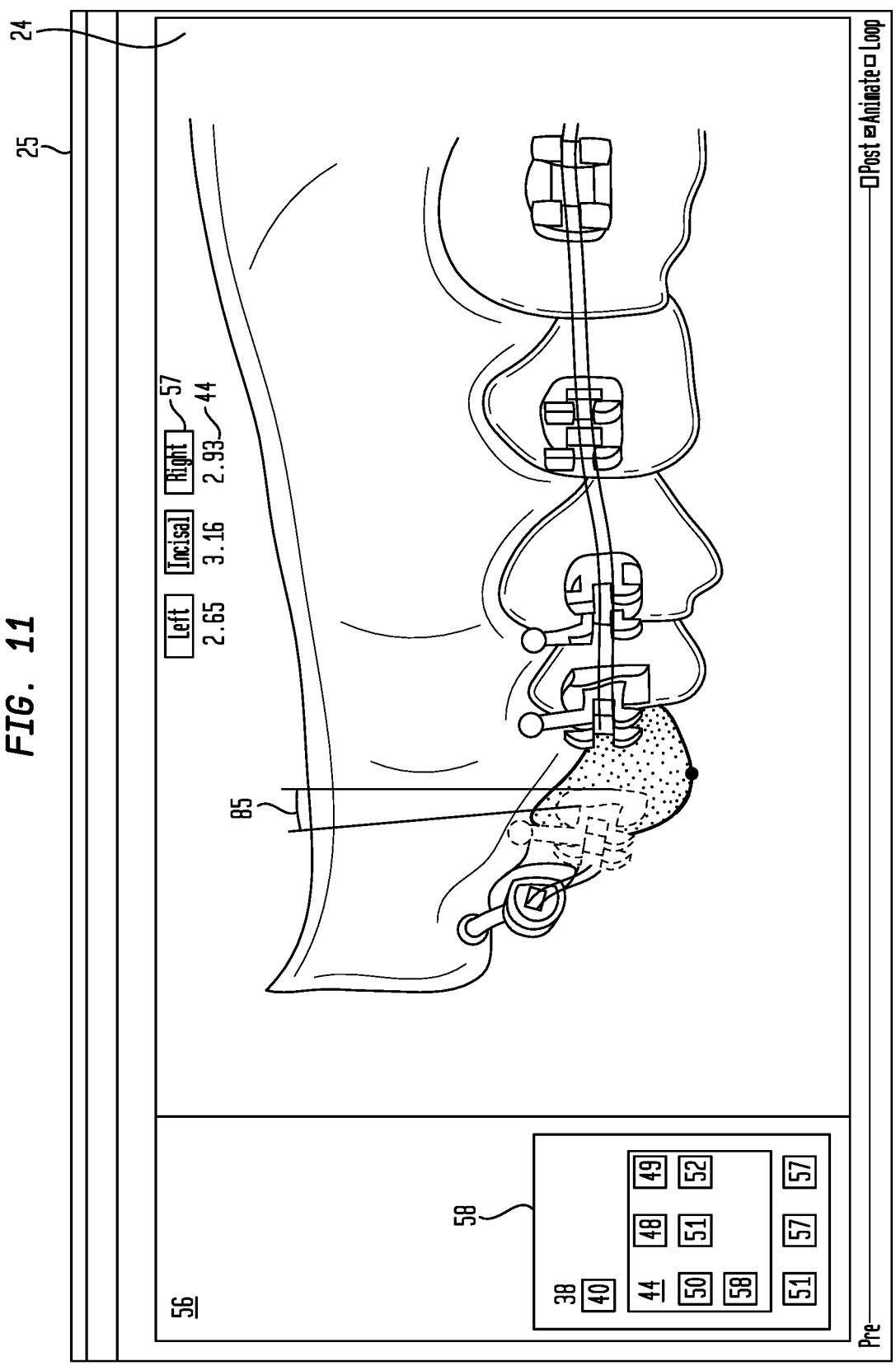
FIG. 11 is an illustration of an embodiment of a graphical user interface which depicts a virtual simulation of the upper arch including a selected and segregated tooth in the upper dental arch moved to the final position allowing selection and placement of a virtual bracket having a bracket base angulation determined by comparison to the initial and prospective buccolingual position of the tooth which in the corresponding orthodontic treatment of the patient's upper dental arch can apply corrective forces to move the tooth from the initial position to the final position shown in the virtual simulation.

Now referring primarily to FIG. 1 and FIGS. 10 and 11, in particular embodiments, the orthodontic treatment application (21) can further include a bracket selection module (65) which can be executed to select a bracket (14) configured to move the segregated selected tooth (39) in the dental arch (8)(8A)(8B) corresponding to movement of the segregated selected tooth (39) from the initial position (10) toward the final position (11) in the virtual dental arch (8)(8A)(8B). The bracket selection module (65) can function to analyze the initial position (10) and the final position (11) of each segregated selected tooth (39) in the virtual dental arch (8)(8A)(8B) in view of virtual bracket locations (61) on the pair of teeth (5) immediately adjacent the segregated selected tooth (39), and by applying tooth movement dependent rules (43), can generate a bracket prescription (68) including a bracket configuration requirement (69) and in cooperation with the bracket location module (65) identify a bracket bonding location (15) for each selected bracket (14) on each segregated selected tooth (39) in the virtual dental arch (8)(8A)(8B).

Now referring primarily to FIGS. 5, 7, 9, 10 and 11, as to particular embodiments, the bracket selection module (65) can function to assess the bracket configuration requirement (69) by determination of a bracket volume (69A) (three-dimensional volume) to be filled by the selected bracket (14) based on the final position (11) of the segregate selected tooth (39). The bracket volume (69A) occurs between the surface of the selected tooth (39) moved to the final position (11) and the depicted location or orientation of the virtual archwire (27) crossing the selected tooth (39). As to certain embodiments, the location or orientation of the virtual archwire (27) crossing the selected tooth (39) may not be depicted, but rather, can be extrapolated based upon the location of the archwire slots (88), or the position of the virtual archwire ends (27A)(27B) of the virtual archwire (27) disposed on the pair of teeth (5A) on either side of the selected tooth (39) (as shown by the illustrative examples of FIGS. 5, 7, and 9). Referring primarily to FIG. 10, a bracket body height (87) can be determined based on the distance between the surface of the selected tooth (39) and the location of the virtual archwire (27) whether depicted or extrapolated. Referring primarily to FIG. 11, the angular position (85) of the bracket base (84) in relation to the bracket body (86) can be determined to afford the correct tooth torquing (49). Generation of force moments related to "tooth tipping (48)", "tooth rotation (50)", "tooth translation (53)", "tooth extrusion (52)" or "tooth intrusion (53)" will be dependent upon execution of the bracket bonding location module (60) which as above described selects the virtual bracket bonding location (61) of the virtual brackets (26) on each segregated selected tooth (39).

Now, referring primarily to FIG. 1, the bracket selection module (65) can then be executed to compare the a bracket configuration requirement (68) to an existing bracket library (70), whether conventionally available from one or a plurality of vendors, or from a bracket combinatorial library (71) including a plurality of brackets (14) each interchangeably fixedly mountable to a corresponding one of a plurality of teeth (5) in the patient's (P) dental arch (6)(6A)(6B). A bracket combinatorial library (71) allows computerized selection between incremental variation in bracket (14) configuration in comparison to the bracket configuration requirement (69) generated by the bracket selection module (65). The bracket selection module (65) can further function to select a bracket (14) from the existing bracket library (70) or bracket combinatorial library (71) which most closely compares to the bracket configuration requirement (68) to generate force moments related to "tooth tipping (48)", "tooth torqueing (49)", "tooth rotation (50)", "tooth translation (53)", "tooth extrusion (52)" or "tooth intrusion (53)" or combinations thereof, for each segregated selected tooth (39) as described in U.S. Pat. No. 9,486,299, hereby incorporated by reference in the entirety herein. In particular embodiments, selection of a bracket (14) from a bracket combinatorial library (71) including a limited number of configurations of brackets (14), the bracket selection module (65) selects the best fit from the bracket combinatorial library (71). The bracket base (84) of the selected bracket (14) having the best fit may not fully contact the surface of the segregated selected tooth (39) moved to the final position (11). The bracket selection module (65) can coordinate with the three-dimensional object production module (72) to correspondingly configure the bonding tray (18) to hold the selected bracket (14) at the correct location to allow additional bonding material (82) to fill the gap between the bracket base (84) and the surface of the segregated selected tooth (39).

Figure 12:
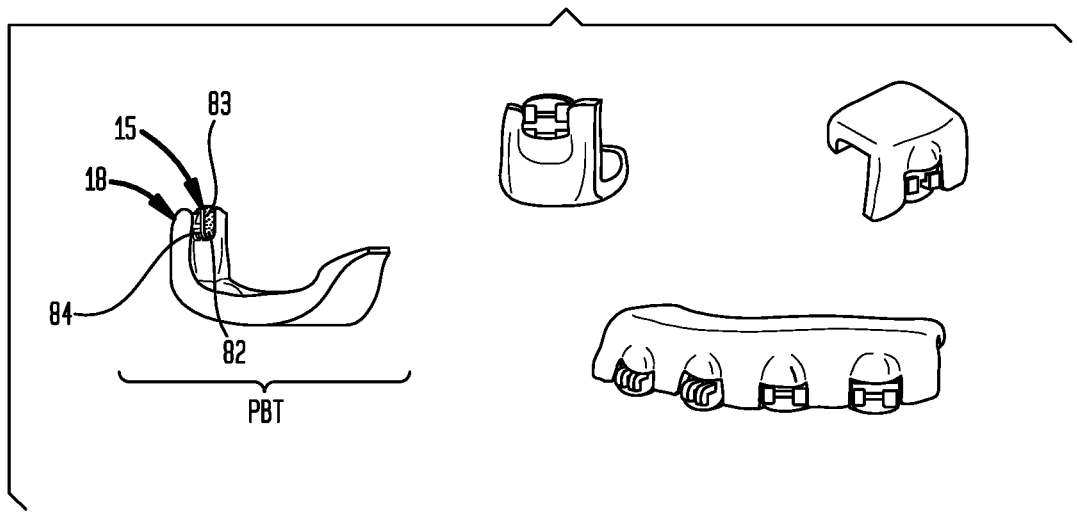
FIG. 12 is an illustration of particular embodiments of the bonding trays produced based upon analysis of the virtual dental arches shown in FIGS. 5, 7, and 9 which hold the selected brackets at locations corresponding to the placement of the virtual brackets on the teeth in the virtual dental arch.
Figure 13:
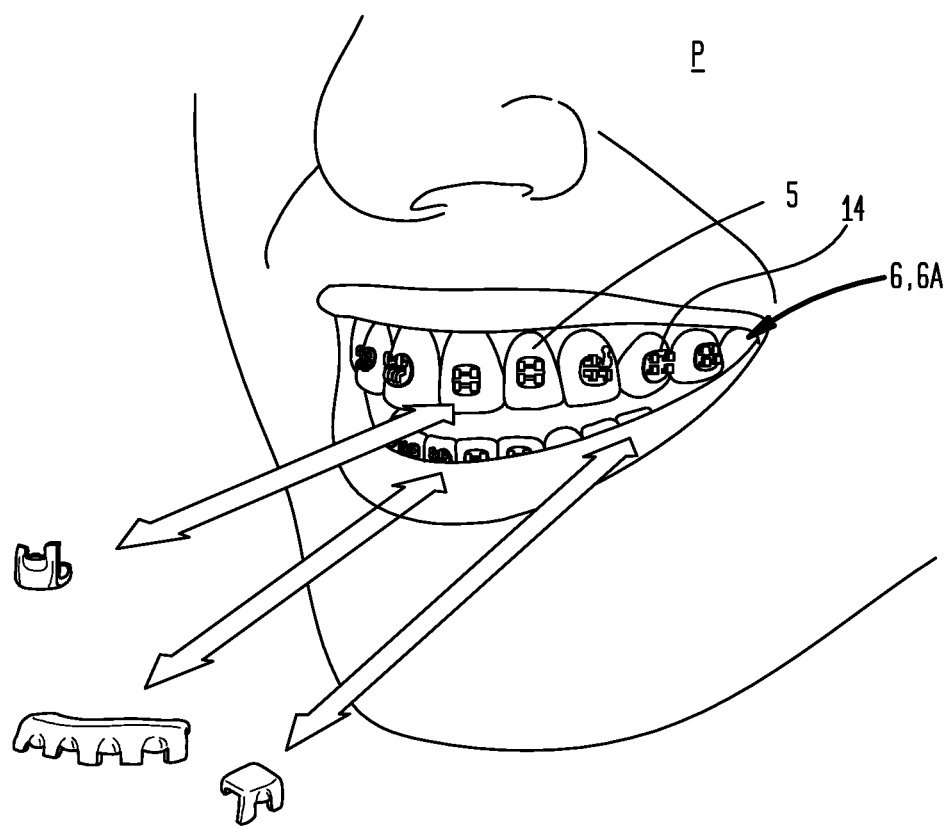
FIG. 13 is an illustration of embodiments of the bonding trays holding the selected brackets for application to the corresponding teeth of a patient at locations corresponding to the placement of the virtual brackets on the teeth in the virtual dental arches shown in FIGS. 5, 7 and 9 and removal of the bonding trays leaving the brackets bonded to the patient's teeth at locations corresponding to the placement of the virtual brackets on the teeth in the virtual dental arch.

Again referring primarily to FIGS. 1 and 12 through 13, in particular embodiments, the orthodontic treatment application (21) can further include a three-dimensional object production module (72) which can be executed to analyze the configuration of the virtual dental arch (8)(8A)(8B), the bracket bonding locations (61) identified by the bracket bonding location module (60), and the selected brackets (14) selected by the bracket selection module (65) to generate one or more digital models (16) of embodiments of the virtual dental arch (8), with or without virtual brackets (26) and embodiments of a bonding tray (18) configured to hold the selected brackets (14) at positions corresponding to the bracket bonding locations (61) identified in the virtual dental arch (8)(8A)(8B). The digital models (16) provide a data representation of the virtual dental arch (8)(8A)(8B) or the bonding tray (18) to be rendered in tangible form by operation of a three-dimensional materials deposition apparatus (73). The digital models (16) can be analyzed by a three-dimensional object production application (74) to generate computer executable instructions to operate the three-dimensional materials deposition apparatus (73) in an additive build up process (75) to produce replica models (17) of embodiments of the virtual dental arch (8)(8A)(8B), or tangible embodiments of a bonding tray (18), or both. The term "additive build up process" for the purposes of this invention means any process of layering materials to produce a three-dimensional object, and without limiting the breadth of the forgoing, particular embodiments of the additive build up process can but need not necessarily include the conventional process referred to as three-dimensional printing ("3D printing") in which the three-dimensional object can be created from a digital model using a materials printer laying down successive layers of a build material or build material and a binder liquid. The term "object" for the purposes of this invention means any configuration of a three-dimensional object and without limiting the breadth of the forgoing includes replica models (17) of a dental arch (8)(8A)(8B) or tangible embodiments of the bonding tray (18), as above described.

Again, referring primarily to FIG. 1, particular embodiments can include a three-dimensional materials deposition apparatus (73) including a materials deposition apparatus controller (76) having a controller processor (77) communicatively coupled to a controller non-transitory computer readable medium (78) containing the three-dimensional object production application (74) and adapted to receive and contain the digital models (16). The digital models (16) can be obtained using CAD/CAM software applications or optical technologies (35) such as three-dimensional scanning systems, as above described. The digital models (16) can be stored in industry-standard file formats as digital model files, which can be transmitted electronically and interpreted by three-dimensional object production application (74) to provide computer program instructions executable to implement functions necessary to control the three-dimensional materials deposition apparatus (73) and additive build up process (75) to produce the replica model (17) or tangible embodiments of the bonding tray (18), as above described. The materials deposition apparatus controller (76) can take the form of a general-purpose computer, special purpose computer or other programmable data processing apparatus.

Again, referring primarily to FIG. 1, as to particular embodiments of the invention, the materials deposition apparatus controller (76) can run the three-dimensional object production application (74) which analyzes the digital model (17), accepts parameter and preference input from the user (33), performs a series of detailed calculations and transmits to the three-dimensional materials deposition apparatus (73) (which as to particular embodiments can be a three-dimensional printer such as, a Form 2 350® material deposition apparatus available from Formlabs, Inc., or a three-dimensional printer assembly as described in U.S. Pat. No. 7,037,382, hereby incorporated by reference herein, or similar apparatus) commands and provides information needed to produce embodiments of the replica model (17) or tangible embodiments of the bonding tray (18).

In particular, the three-dimensional object production application (74) may allow the user (33) to arrange one or more digital models (17) in a virtual volume representing the actual fabrication space within the three-dimensional materials deposition apparatus (73). The three-dimensional object production application (74) can then slice the array of digital models (17) into a plurality of layers, each of a predetermined thickness, which are transmitted to control electronics (78) housed within the three-dimensional materials deposition apparatus (73).

Particular embodiments of the three-dimensional materials deposition apparatus (73) can, but need not necessarily, comprise a three-dimensional printer having an array of jet type print heads which deposit a binder liquid (79) onto successive layers of a build material (80). Where the binder liquid (79) combines with the build material (80), typically, a powder build material (80) reacts with the binder liquid (79) and hardens. By controlling the placement of binder liquid (79) from these print heads, the configuration of the replica model (17) or the tangible bonding tray (18) can be physically reproduced by an additive build up process (75). Further details of binding a build material (80) with a binder liquid (79) to form three-dimensional objects such as a replica model (17) or tangible embodiments of a bonding tray (18) are disclosed in U.S. Pat. Nos. 5,340,656 and 5,387,380, hereby incorporated by reference herein.

In particular embodiments, the build material (80) can comprise methacrylic acid esters, or a combination of methacrylic acid esters and phosphine oxides as a photoinitiator which exposed to ultraviolet light initiates hardening of the methacrylic acid esters, for example, Dental SG Resin liquid available from Formlabs, Inc. comprises a suitable build material (80). A three-dimensional object of the present invention including embodiments of the replica model (17) of dental arch (8)(8A)(8B) or tangible embodiments of the bonding tray (18) may be produced from these build materials (80) using, for example, a three-dimensional printing system similar to various embodiments of U.S. Pat. Nos. 6,658,314, 7,604,768 and 7,500,846, each hereby incorporated by reference.

In particular embodiments, the build material (80) can comprise a plastic filament (81). The plastic filament can, for example, comprise acrylonitrile butadiene styrene (ABS) or polylactic acid (PLA) provided as strands of filament of about one millimeter to about three millimeters in diameter that unwind from a coil or spool. The three-dimensional materials deposition apparatus (73) can comprise a fused deposition modeling (FDM) or, more generally, fused filament fabrication (FFF) printer. The plastic filament can be supplied to a print head with an extrusion nozzle, such as, a gear which pulls the plastic filament off the spool and into the extrusion nozzle. The extrusion nozzle can be adapted to turn its flow on and off. The extrusion nozzle (or an upstream portion of the print head) is heated to melt the plastic filament as it is passed into, or through, the extrusion nozzle so that it liquefies. The pointed extrusion nozzle deposits the liquefied material in ultrafine lines (for example, in lines that are about 0.1 millimeters across).

As to particular embodiments, the build material(s)(80) used in the three-dimensional printing (or other forming or fabrication process) of the bonding trays (18), when cured can, but need not necessarily, have Shore A hardness which falls in a wide range of Shore A hardness. The Shore A hardness can, as an example, be between about 50 to about 90. Similarly, the tensile strength of the matrix material (22) can be between about $1.0 \times 10^6$ Pa to about $5.0 \times 10^6$ Pa. However, the above illustrative Shore A hardness or tensile strength is not intended to preclude embodiments which fall outside of these ranges.

Now referring primarily to FIGS. 1 and 12 through 13, particular embodiments of the method, can further include applying a bonding material (82) to the bottom surface (83) of the bracket base (84) of each of the selected brackets (14) retained in the bonding tray (18). As above described, the bonding tray (18) holds the selected brackets (14) corresponding to the segregated selected teeth (39) in the virtual dental arch (8), which in certain instance can be only one tooth, or can be only two adjacent or non-adjacent teeth or any number and positioning of segregated selected teeth (5A) in the virtual dental arch (8)(as show in the example of FIG. 11)(partial bonding tray (PBT), positioning the bonding tray (18) (which retains selected brackets (14)) to the corresponding plurality of teeth (5) of the dental arch (6)(6A)(6B), and concurrently seating the selected brackets (14) to the plurality of teeth (5) in the dental arch (6)(6A)(6B)(as shown in the example of FIG. 12). The seating of the selected brackets (14) to the plurality of teeth (5) in the dental arch (6) can substantially correspond to the locations of the virtual brackets (26) on the selected one or more of the virtual plurality of teeth (5A) in the virtual dental arch (8)(8A)(8B). The method further includes removing the bonding tray (18) from the selected brackets (14) leaving the selected brackets (14) bonded to the one or more teeth in the dental arch (6).

As can be easily understood from the foregoing, the basic concepts of the present invention may be embodied in a variety of ways. The invention involves numerous and varied embodiments of an orthodontic treatment system and methods for making and using such orthodontic treatment system including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "three-dimensional printer" should be understood to encompass disclosure of the act of "three-dimensional printing"—whether explicitly discussed or not—and, conversely, were there effectively disclosure of the act of "three-dimensional printing", such a disclosure should be understood to encompass disclosure of a "three-dimensional printer" and even a "means for three-dimensional printing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the orthodontic treatment systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A system for correcting malocclusion of teeth, comprising:
    a processor communicatively coupled to a non-transitory memory containing computer program executable to:
        convert captured images of a dental arch including a plurality of teeth fitted with existing braces interconnected by an existing archwire into a virtual dental arch including a plurality of virtual teeth fitted with virtual braces interconnected by a virtual archwire presented on a display surface of a display device;

segregate each of said plurality of virtual teeth in said virtual dental arch to allow independent movement of a virtual tooth in said virtual dental arch;

remove said virtual braces from said virtual tooth;

move said virtual tooth within said plurality of virtual teeth from an initial position in said virtual dental arch to a final position in said virtual dental arch;

identify a virtual bracket bonding location on said virtual tooth in said virtual dental arch based on movement of said virtual tooth from said initial position to said final position in said virtual dental arch;

determine a three-dimension bracket volume to be filled by a virtual bracket at said virtual bracket bonding location with said virtual tooth in said final position in said virtual dental arch, said three-dimensional bracket volume delimited by a surface of said virtual tooth in said final position in said virtual dental arch and a location of:

said virtual archwire crossing said virtual tooth; or said location of said virtual archwire crossing said virtual tooth extrapolated based upon a location of virtual archwire slots of said virtual braces on a pair of virtual teeth disposed on either side of said virtual tooth; or said location of said virtual archwire crossing said virtual tooth extrapolated based upon position of virtual archwire ends of said virtual archwire of said virtual braces on a pair of virtual teeth disposed on either side of said virtual tooth; and select a bracket from a plurality of brackets based on determination of said three-dimension bracket volume; and generate a digital model of a bonding jig configured to hold the selected bracket at said virtual bonding location on said virtual tooth; and a three-dimensional materials deposition apparatus configured to fabricate the bonding jig based on the digital model of the bonding jig.

2. The computer system of claim 1, wherein said computer executable instructions further executable to directly position said virtual tooth in said virtual dental arch from said initial position in said virtual dental arch to said final position in said virtual dental arch based on entry of malocclusion correction values into malocclusion correction value cells.

3. The computer system of claim 1, wherein said computer executable instructions further executable to present one or more virtual tooth positioning control elements on said display surface of said display device, said one or more virtual tooth positioning control elements operable to position said virtual tooth in said virtual dental arch from said initial position in said virtual dental arch to said final position in said virtual dental arch.

4. The computer system of claim 1, wherein said three-dimension bracket volume of said virtual bracket at said virtual bracket bonding location with said virtual tooth in said final position in said virtual dental arch defines:

a virtual bracket body height of a virtual bracket body based on a distance between said surface of said virtual tooth in said virtual dental arch at said final position and the location of said virtual archwire crossing said virtual tooth or said location of said virtual archwire extrapolated based upon location of said virtual archwire slots of said virtual braces on a pair of virtual teeth disposed on either side of said virtual tooth or said position of said virtual archwire ends of said virtual archwire of said virtual braces on said pair of virtual teeth disposed on either side of said virtual tooth, or a virtual bracket base angulation in relation to said virtual bracket body based on angulation of said surface of said virtual tooth at said final position in said virtual dental arch.

5. The computer system of claim 1, wherein said wherein said plurality of brackets comprises a bracket library having a limited number of bracket configurations.

6. A method of correcting malocclusion of teeth comprising:

obtaining images of a dental arch including a plurality of teeth fitted with braces interconnected by an archwire;

converting said images of a dental arch including said plurality of teeth fitted with braces into a virtual dental arch including a plurality of virtual teeth fitted with virtual braces interconnected by a virtual archwire presented on a display surface of a display device;

segregating movement of each of said plurality of virtual teeth in said virtual dental arch to allow independent movement of a virtual tooth in said virtual dental arch;

removing said virtual braces from a virtual tooth;

moving, based on user interaction with said system, said virtual tooth from an initial position to a final position in said virtual dental arch;

identifying a virtual bracket bonding location on said virtual tooth in said virtual dental arch based on movement of said virtual tooth from said initial position to said final position in said virtual dental arch;

determining a three-dimension bracket volume to be filled by a virtual bracket at said virtual bracket bonding location with said virtual tooth in said final position in said virtual dental arch, said three dimensional bracket volume delimited by a surface of said virtual tooth in said final position in said virtual dental arch and a location of:

said virtual archwire crossing said virtual tooth; or said location of said virtual archwire crossing said virtual tooth extrapolated based upon a location of virtual archwire slots of said virtual braces on a pair of virtual teeth disposed on either side of said virtual tooth; or said location of said virtual archwire crossing said tooth extrapolated based upon position of virtual archwire ends of said virtual archwire of said virtual braces on a pair of virtual teeth disposed on either side of said virtual tooth;

selecting a bracket from a plurality of brackets based on determination of said three-dimension bracket volume; and bonding said bracket selected from said plurality of brackets to a physical tooth.

7. The method of claim 6, further comprising generating a bonding jig specification to operate a three-dimensional materials deposition apparatus, said bonding jig specification configured to operate said three-dimensional materials deposition apparatus to build up a bonding jig configured to hold said bracket at said bonding location identified on said virtual tooth.

8. The method of claim 7, further comprising operating said three-dimensional materials deposition apparatus to produce said bonding jig corresponding to said bonding jig specification.

9. The method of claim 6, further comprising directly positioning said virtual tooth in said virtual dental arch presented on said display surface of said display device from said initial position in said virtual dental arch to said final position in said virtual dental arch based on entry of malocclusion correction values into malocclusion correction value cells.

10. The method of claim 9, wherein said three-dimension bracket volume of said virtual bracket at said virtual bracket bonding location with said virtual tooth in said final position in said virtual dental arch defines:

a virtual bracket body height of a virtual bracket body based on a distance between said surface of said virtual tooth in said virtual dental arch at said final position and the location of said virtual archwire crossing said virtual tooth or said location of said virtual archwire extrapolated based upon location of said virtual archwire slots of said virtual braces on a pair of virtual teeth disposed on either side of said virtual tooth or said position of said virtual archwire ends of said virtual archwire of said virtual braces on said pair of virtual teeth disposed on either side of said virtual tooth, or a virtual bracket base angulation in relation to said virtual bracket body based on angulation of said surface of said virtual tooth at said final position in said virtual dental arch.

11. The method of claim 6, further comprising presenting one or more virtual tooth positioning control elements on said display surface of said display device.

12. The method of claim 11, further comprising operating said one or more virtual tooth positioning control elements to position said virtual tooth in said virtual dental arch from said initial position in said virtual dental arch to said final position in said virtual dental arch.

13. The method of claim 12, further comprising presenting said virtual dental arch on said display surface of said display device based on said final position of said virtual tooth in said virtual dental arch.

14. The method of claim 11, wherein said plurality of brackets comprises a bracket library having a limited number of bracket configurations.

* * * * *